US012616484B2

(12) United States Patent
Alrasheed et al.

(10) Patent No.: US 12,616,484 B2
(45) Date of Patent: May 5, 2026

(54) DUAL-HEADED SURGICAL INSTRUMENT

(71) Applicant: KING SAUD UNIVERSITY, Riyadh (SA)

(72) Inventors: Abdulaziz Saleh Alrasheed, Riyadh (SA); Sherif Mohammed Elseufy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/764,087

(22) Filed: Jul. 3, 2024

(65) Prior Publication Data

US 2026/0007416 A1     Jan. 8, 2026

(51) Int. Cl.
*A61B 17/16* (2006.01)
*A61B 17/00* (2006.01)
*A61B 17/32* (2006.01)

(52) U.S. Cl.
CPC ..................... *A61B 17/1659* (2013.01); *A61B 2017/00353* (2013.01); *A61B 2017/320008* (2013.01); *A61B 2017/320044* (2013.01)

(58) Field of Classification Search
CPC .... A61B 17/1659; A61B 2017/320044; A61C 3/00
See application file for complete search history.

(56) References Cited

U.S. PATENT DOCUMENTS

| | | | |
|---|---|---|---|
| D225,621 S | 12/1972 | Malkovich | |
| 5,269,796 A | 12/1993 | Miller et al. | |
| D405,179 S | 2/1999 | Kirsch et al. | |
| 9,550,057 B2 | 1/2017 | Papay et al. | |
| 10,555,794 B2 | 2/2020 | Lee | |
| 2017/0296308 A1* | 10/2017 | Lee | A61C 8/0006 |
| 2020/0237485 A1* | 7/2020 | Pineyro | A61C 8/0056 |

FOREIGN PATENT DOCUMENTS

| | | |
|---|---|---|
| CN | 3168934 | 12/2000 |
| CN | 203468731 U | 3/2014 |

OTHER PUBLICATIONS

"Cottle Septum Elevator", NewMed Instruments, Apr. 19, 2024, https://new-medinstruments.com/dissectors-and-elevators/Cottle-Septum-Elevator.html.

* cited by examiner

*Primary Examiner* — Andrew Yang
(74) *Attorney, Agent, or Firm* — Nath, Goldberg & Meyer; Joshua B. Goldberg

(57) ABSTRACT

The dual-headed surgical instrument is a surgical instrument with tool heads at either end for performing surgical procedures, such as, for example, skull base dissection. The dual-headed surgical instrument includes an elongated handle portion extending along a longitudinal axis. The elongated handle portion has opposed first and second ends. The first end of the elongated handle portion has a first surgical tool head and the second end of the elongated handle portion has a second surgical tool head. The first surgical tool head extends along a first tool axis which is angularly displaced from the longitudinal axis by 60°. The second surgical tool head extends along a second tool axis which is angularly displaced from the longitudinal axis by 150°. The first end of the elongated handle portion may be curved to define the 60° angle of the first tool axis.

4 Claims, 2 Drawing Sheets

DUAL-HEADED SURGICAL INSTRUMENT

BACKGROUND

Field

The disclosure of the present patent application relates to surgical instruments, and particularly to a dual-headed surgical instrument with tool heads at either end for performing surgical procedures, such as skull base dissection.

Description of Related Art

Endoscopic skull base surgery (ESBS) is widely used for accessing certain tumors of the skull base. In ESBS, access is typically achieved directly through the nose and paranasal sinuses, although access through the eye socket may also be achieved with the endoscope. The anatomy of the skull base is complex, with access to different regions being characterized by a number of different angles extending from the frontal sinus to the craniocervical junction. As such, ESBS requires the surgeon to perform a variety of difficult maneuvers in order to safely perform surgical resection and subsequent reconstruction. In order to access the multiple locations, a surgeon is typically required to switch instruments multiple times throughout the procedure, with each instrument being adapted for a specific access angle. Minimizing the number of instruments used during surgery is important in order to decrease the overall duration of surgery and also to minimize complexity, thus reducing the possibility of error or accident during the procedure. Thus, a dual-headed surgical instrument solving the aforementioned problems is desired.

SUMMARY

The dual-headed surgical instrument is a surgical instrument with tool heads at either end for performing surgical procedures, such as, for example, skull base dissection. The dual-headed surgical instrument includes an elongated handle portion extending along a longitudinal axis. The elongated handle portion has opposed first and second ends. The first end of the elongated handle portion has a first surgical tool head and the second end of the elongated handle portion has a second surgical tool head. The first surgical tool head extends along a first tool axis which is angularly displaced from the longitudinal axis by 60°. The second surgical tool head extends along a second tool axis which is angularly displaced from the longitudinal axis by 150°. The first end of the elongated handle portion may be curved to define the 60° angle of the first tool axis. In one embodiment, each of the first and second surgical tool heads is a dissector tool head. In an alternative embodiment, the first surgical tool head is a dissector tool head and the second surgical tool head is a scoop.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
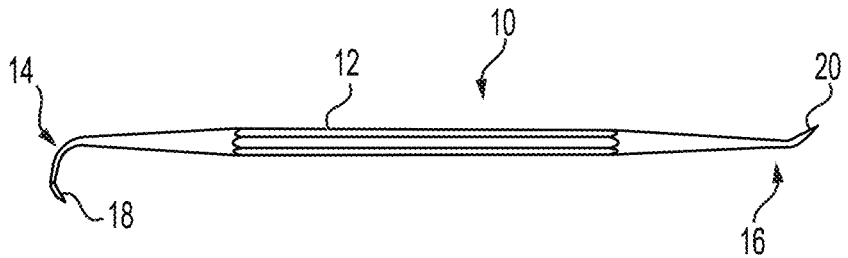
FIG. 1 is a side view of a dual-headed surgical instrument.
Figures 2A, 2B:
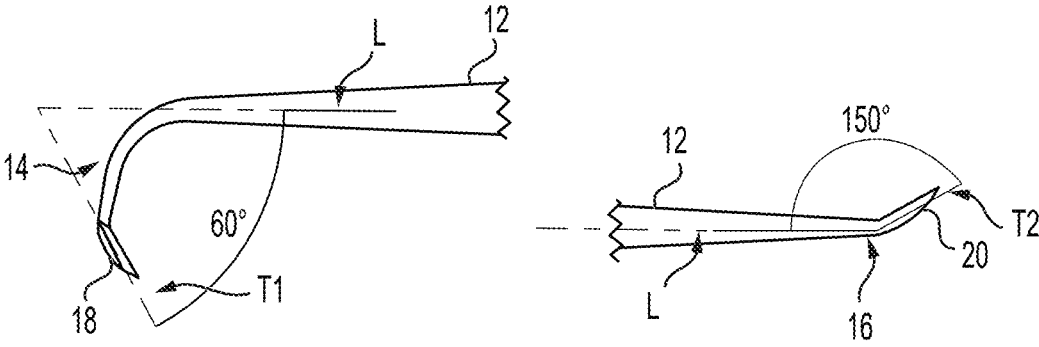
FIG. 2A is a partial side view of the dual-headed surgical instrument.
FIG. 2B is a partial side view of the dual-headed surgical instrument.

The dual-headed surgical instrument 10 is a surgical instrument with tool heads at either end for performing surgical procedures, such as, for example, skull base dissection. As shown in FIGS. 1, 2A and 2B, the dual-headed surgical instrument 10 includes an elongated handle portion 12 extending along a longitudinal axis L. The elongated handle portion 12 has opposed first and second ends 14, 16, respectively. The first end 14 of the elongated handle portion 12 has a first surgical tool head 18 and the second end 16 of the elongated handle portion 12 has a second surgical tool head 20. As best seen in FIG. 2A, the first surgical tool head 18 extends along a first tool axis T1 which is angularly displaced from the longitudinal axis L by 60°. As best seen in FIG. 2B, the second surgical tool head 20 extends along a second tool axis T2 which is angularly displaced from the longitudinal axis L by 150°. As shown, the first end 14 of the elongated handle portion 12 may be curved to define the 60° angle of the first tool axis T1.

It should be understood that the dual-headed surgical instrument 10 may be formed of any suitable type of material, such as surgical stainless steel or the like. It should be further understood that the first and second tool heads 18, 20 may be any suitable type of surgical tool heads. In the non-limiting example of FIGS. 1, 2A and 2B, each of the first and second surgical tool heads 18, 20 is a dissector tool head. As a non-limiting example, the dual-headed surgical instrument 10 may be used for skull base dissection. In this non-limiting example, the 150° angle of the second tool head 20 allows the surgeon to reach the middle and posterior cranial fossa, and the 60° angle of the first tool head 18 allows the surgeon to reach the anterior cranial fossa. Thus, the first and second ends 14, 16 allow access to different areas of the skull base and cover approximately 180° from the angles of the base of the skull.

Figure 3:
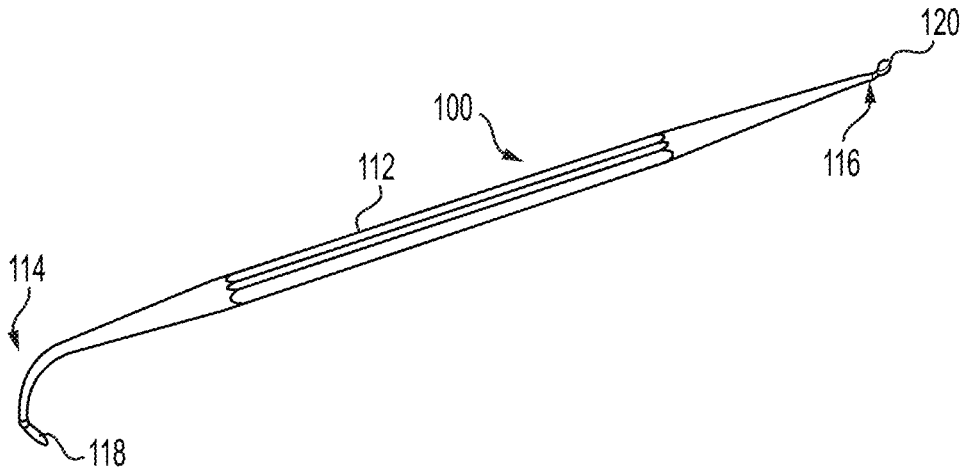
FIG. 3 is a side view of an alternative embodiment of the dual-headed surgical instrument.
Figure 4A:
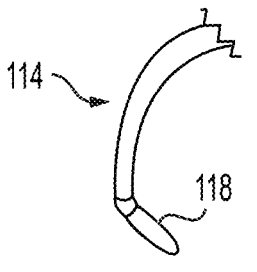
FIG. 4A is a partial side view of the dual-headed surgical instrument of FIG. 3.
Figure 4B:
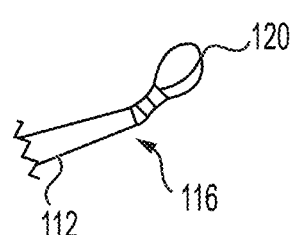
FIG. 4B is a partial side view of the dual-headed surgical instrument of FIG. 3.

In the alternative embodiment of FIGS. 3, 4A and 4B, the dual-headed surgical instrument 100 is similar to the dual-headed surgical instrument 10 described above, including an elongated handle portion 112 extending along a longitudinal axis and having opposed first and second ends 114, 116, respectively. The first end 114 of the elongated handle portion 112 has a first surgical tool head 118 and the second end 116 of the elongated handle portion 112 has a second surgical tool head 120. As in the previous embodiment, the first surgical tool head 118 extends along a first tool axis which is angularly displaced from the longitudinal axis by 60°. Similarly, the second surgical tool head 120 extends along a second tool axis which is angularly displaced from the longitudinal axis by 150°. In the non-limiting example of FIGS. 4A and 4B, the first surgical tool head 118 is a dissector tool head and the second surgical tool head 120 is a scoop.

It is to be understood that the dual-headed surgical instrument is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A dual-headed surgical instrument, comprising:

an elongated handle portion extending along a longitudinal axis, the elongated handle portion having opposed first and second ends, wherein the first end has a first surgical tool head, said first surgical tool head comprising a flat surface having a semi-sharp peripheral edge and an opposing atraumatic face;

wherein the second end has a second surgical tool head, said second surgical tool head comprising either a flat surface having a semi-sharp peripheral edge and an opposing atraumatic face or a concave elliptical surface having a semi sharp peripheral edge, wherein the first surgical tool head extends along a first tool axis, the first tool axis being angularly displaced from the longitudinal axis by 60°±2° such that the first surgical tool head is configured to reach an anterior cranial fossa of a patient, wherein the second surgical tool head extends along a second tool axis, the second tool axis being angularly displaced from the longitudinal axis by 150°±2° such that the second surgical tool head is configured to reach both a middle cranial fossa and a posterior crania fossa of the patient, wherein the first end of the elongated handle portion is curved with respect to the longitudinal axis, wherein the second end of the elongated handle portion is straight with respect to the longitudinal axis, wherein the first surgical tool head is attached the first end of the elongated handle portion that is curved with respect to the longitudinal axis, and wherein the second surgical tool head is attached the second end of the elongated handle portion that is straight with respect to the longitudinal axis.

2. The dual-headed surgical instrument as recited in claim 1, wherein each of the first and second surgical tool heads comprises a dissector tool head.

3. The dual-headed surgical instrument as recited in claim 1, wherein the first surgical tool head comprises a dissector tool head.

4. The dual-headed surgical instrument as recited in claim 3, wherein the second surgical tool head comprises a scoop having said concave elliptical surface with said semi sharp peripheral edge.

* * * * *